(12) United States Patent
Deng et al.

(10) Patent No.: US 10,231,651 B2
(45) Date of Patent: Mar. 19, 2019

(54) GAIT AUTHENTICATION SYSTEM AND METHOD THEREOF

(71) Applicant: BAE Systems Information And Electronic Systems Integration Inc., Nashua, NH (US)

(72) Inventors: Yunbin Deng, Westford, MA (US); Yu Zhong, Winchester, MA (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 656 days.

(21) Appl. No.: 14/835,258

(22) Filed: Aug. 25, 2015

(65) Prior Publication Data

US 2018/0078179 A1 Mar. 22, 2018

Related U.S. Application Data

(60) Provisional application No. 62/055,298, filed on Sep. 25, 2014.

(51) Int. Cl.
*G05B 19/00* (2006.01)
*A61B 5/117* (2016.01)
(Continued)

(52) U.S. Cl.
CPC .............. *A61B 5/117* (2013.01); *A61B 5/112* (2013.01); *A61B 5/6898* (2013.01);
(Continued)

(58) Field of Classification Search
CPC ....... A61B 5/117; A61B 5/112; A61B 5/6898; A61B 2562/0219; G06K 9/00348; H04L 63/083; H04W 12/06
(Continued)

(56) References Cited

U.S. PATENT DOCUMENTS 9,943,250 B2 * 4/2018 Plotnik-Peleg ........ A61B 5/744
2012/0095722 A1 * 4/2012 Ten Kate .............. A61B 5/1117
702/141

(Continued)

OTHER PUBLICATIONS

Deng, Y. and Zhong, Y., Sensor Orientation Invariant Mobile Gait Biometrics, IEEE International Joint Conference on Biometrics, Clearwater, FL, Sep. 29-Oct. 2, 2014.
(Continued)

*Primary Examiner* — Zhen Y Wu
(74) *Attorney, Agent, or Firm* — Sand, Sebolt & Wernow LPA; Scott J. Asmus

(57) ABSTRACT

A gait authentication system and method is provided. The system includes a mobile computing device configured to be carried by a person while moving with a unique gait. A first sensor (e.g. an accelerometer) is carried by the mobile computing device and generates a first signal. A second sensor (e.g. a gyroscope) is carried by the mobile computing device and generates a second signal. A gait dynamics logic implements an identity vector (i-vector) approach to learn feature representations from a sequence of arbitrary feature vectors carried by the first and second signals. In the method for real time gait authentication, the computing of invariant gait representations are robust to sensor placement while preserving highly discriminative temporal and spatial gait dynamics and context.

21 Claims, 5 Drawing Sheets

(51) Int. Cl.
    A61B 5/11     (2006.01)
    A61B 5/00     (2006.01)
    H04L 29/06    (2006.01)
    G06K 9/00     (2006.01)
    H04W 12/06    (2009.01)
(52) U.S. Cl.
    CPC ........ *G06K 9/00348* (2013.01); *H04L 63/083* (2013.01); *H04L 63/0861* (2013.01); *H04W 12/06* (2013.01); *A61B 2562/0219* (2013.01)
(58) Field of Classification Search
    USPC ..................................................... 340/5.82
    See application file for complete search history.

(56) References Cited

U.S. PATENT DOCUMENTS

| | | | | |
|---|---|---|---|---|
| 2013/0324888 | A1* | 12/2013 | Solinsky | A61B 5/112 600/595 |
| 2014/0089673 | A1* | 3/2014 | Luna | H04L 63/0861 713/186 |
| 2014/0303508 | A1* | 10/2014 | Plotnik-Peleg | A61B 5/744 600/483 |
| 2015/0112603 | A1 | 4/2015 | Zhong | |
| 2015/0112899 | A1* | 4/2015 | Dagum | A61B 5/6898 706/12 |
| 2016/0192863 | A1* | 7/2016 | Zhong | A61B 5/112 600/595 |

OTHER PUBLICATIONS

Aminian, K. et al., Spatio-temporal parameters of gait measured by an ambulatory system using miniature gyroscopes, Journal of Biomechanics35, No. 5 (2002): 689-699.
Bachlin, M. et al., Quantifying gait similarity: user authentication and real-world challenge, Advances in Biometrics, 2009.
Bao, L. and Intille, S., Activity recognition from user-annotated acceleration data, Pervasive Computing, pp. 1-17, Spring Berlin Heidelberg, 2004.
Cutler, R.G. and Davis, L.S., Robust real-time periodic motion detection, analysis and applications, IEEE Trans. Pattern Analysis and Machine Intelligence, 22(8), 2000.
Dehak, N. et al., FrontEnd Factor Analysis for Speaker Verification, IEEE Trans. Audio, Speech, and Lang. Proc., 19(4), 2011.
Derawi, M.O., Accelerometer-based gait analysis, a survey, Norwegian Information Security Conf., pp. 33-44, 2010.
Derawi, M.O. et al., Improved cycle detection for accelerometer based gait authentication, 6th IEEE Int'l Conf., Intelligent Information Hiding and Multimedia Signal Processing (IIH-MSP), 2010.
Gafurov, D., Biometric gait authentication using accelerometer sensor, JCP, 1(7), 2006.
Gafurov, D. et al., Improved gait recognition performance using cycle matching, IEEE 24th Int'l Conf. Advanced Information Networking and Applications Workshops (WAINA), 2010.
Iso, T. and Yamazaki, K., Gait analyzer based on a cell phone with a single three-axis accelerometer, the 8th Conf. on Human-computer interaction with mobile devices and services, pp. 141-144, 2006.
Jain, A.K. et al., Biometrics: Personal Identification in Networked Society, Kluwer Academic Publishers, 1999. (reference to follow).
Jain, A.K. et al., Biometrics: a grand challenge, Proc. Int'l Conf. on Pattern Recognition, vol. 2, pp. 935-942, 2004.
Kale, A. et al., Gait analysis for human identification, Audio-and Video-Based Biometric Person Authentication, pp. 706-714. Spring Berlin Heidelberg, 2003.
Kobayashi, T. et al., Rotation invariant feature extraction from 3-d acceleration signals, Int'l Conf. on Acoustics, Speech, and Signal Processing, 2011.
Kwapisz, J.R. et al., Cell phone-based biometric identification, Biometrics: 4th IEEE Int'l Conf. Theory Applications and Systems (BTAS), 2010.
Lee, L. and Grimson, W.E.L., Gait analysis for recognition and classification. In Proc. 5th IEEE INt'l Conf. Automatic Face and Gesture Recognition, pp. 148-155, 2002.
Liu, R. et al., A wearable acceleration sensor system for gait recognition, 2nd IEEE Conf. Industrial Electronics and Applications, 2007.
Mantyjarvi, J. et al., Identifying users of portable devices from gait pattern with accelerometers, IEEE Int'l Conf. Acoustics, Speech, and Signal Processing, vol. 2, 2005.
Ngo, T.T. et al., The Largest Inertial Sensor-based Gait Database and Performance Evaluation of Gait Recognition, Pattern Recognition, 47(1), pp. 228-237, Jan. 2014.
Pan, G. et al., Accelerometer-based gait recognition via voting by signature points. Electronics letters 45(22): 1116-1118, 2009.
Povey, D. et al., The Kaldi speech recognition toolkit, Proc. IEEE ASRU, 2011.
Sarkar, S. et al., The humanID gait challenge problem: Data sets, performance, and analysis. IEEE Trans. Pattern Analysis and Machine Intelligence, 27(2): 162-177, 2005.
Sprager, S., A cumulant-based method for gait identification using accelerometer data with principal component analysis and support vector machine; Sensors, Signals, Visualization, Imaging, Simulation, and Materials, pp. 94-99, 2009.
Juefei-Xu, F. et al., Gait-ID on the move: Pace independent human identification using cell phone accelerometer dynamics, IEEE Fifth Int'l Conf. on Biometrics: Theory, Applications and Systems (BTAS), pp. 8-15, 2012.
Jain, A.K. et al., Biometrics: Personal Identification in Networked Society, pp. 43-64, Kluwer Academic Publishers, 1999.

* cited by examiner

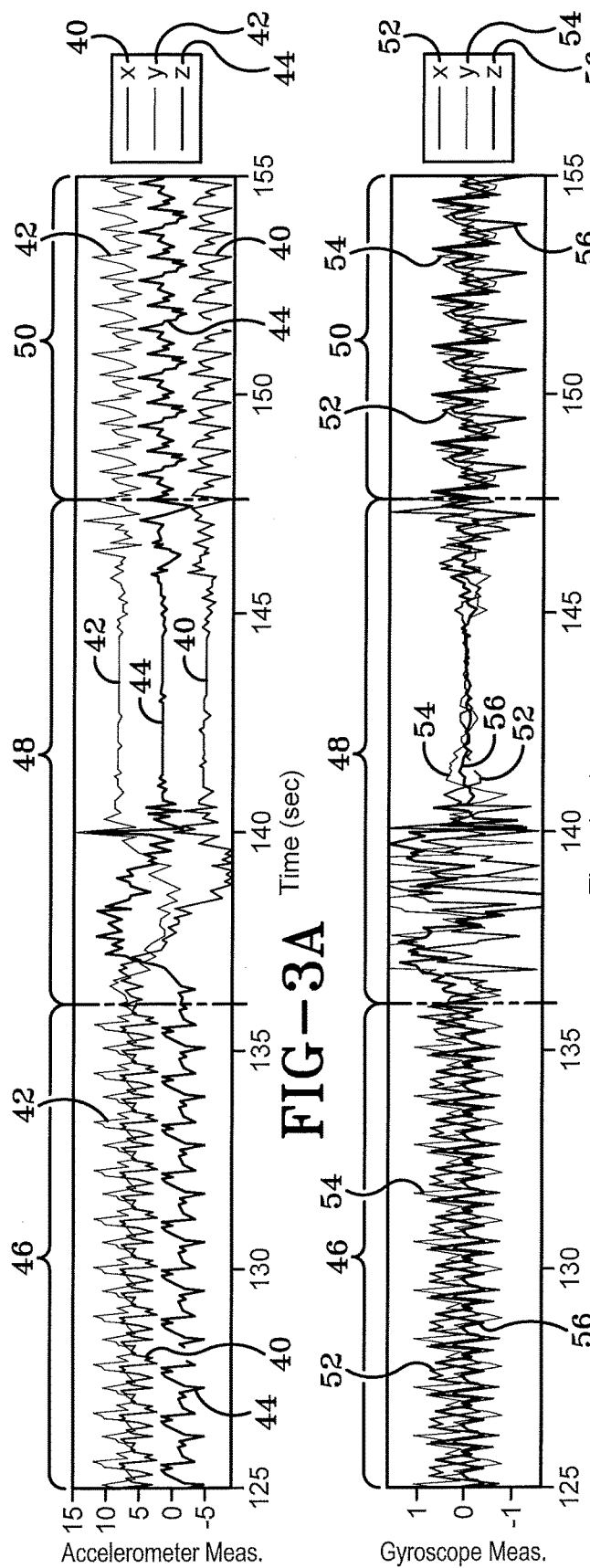
FIG-3A
FIG-3B
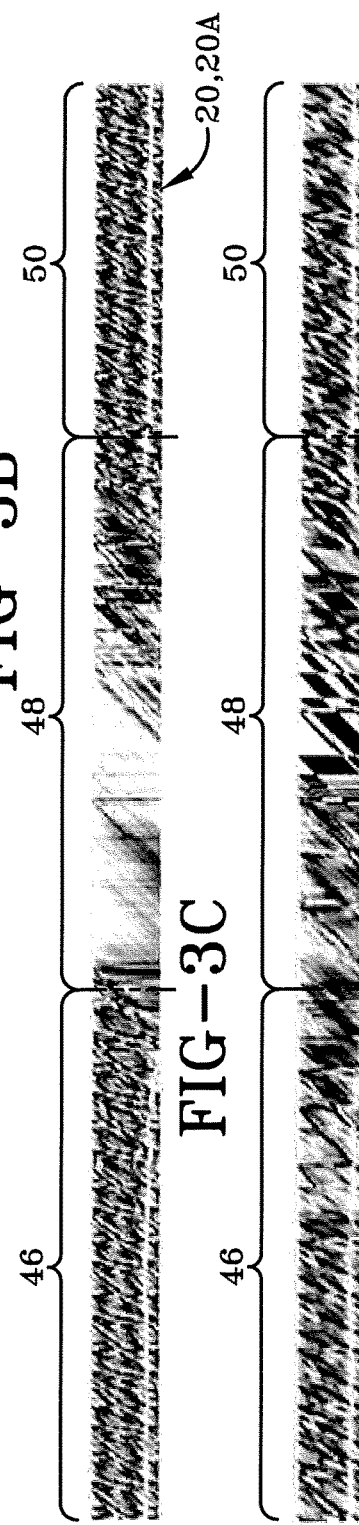
FIG-3C
FIG-3D

| Approach | Sensor Modality | | |
|---|---|---|---|
| | Accelerometer | Gyroscope | Fused |
| 60 — Gafurov et al | 15.8 | NA | NA |
| 62 — Derawi et al | 14.3 | NA | NA |
| 64 — Liu et al | 14.3 | NA | NA |
| 66 — Ngo et al | 13.5 | 20.2 | NA |
| 68 — Inp GDI + i-vector | 8.9 | 11.3 | 7.1 |
| 70 — NC GDI + i-vector | 6.8 | 10.9 | 5.6 |
| 72 — System Fusion | 5.5 | 9.3 | 5.0 |

GAIT AUTHENTICATION SYSTEM AND METHOD THEREOF

CROSS REFERENCE TO RELATED APPLICATIONS

This disclosure claims the benefit of and priority to U.S. Provisional Application Ser. No. 62/055,298, filed on Sep. 25, 2014; the entirety of which is hereby incorporated by reference as if fully re-written.

STATEMENT OF GOVERNMENT INTEREST

This disclosure was made with United States Government support under Contract No. FA8750-13-C-0225 awarded by U.S. Air Force. The United States Government has certain rights in this disclosure.

BACKGROUND

Technical Field

The present disclosure relates generally to authentication of persons. More particularly, the disclosure relates to gait authentication. Specifically, the present disclosure relates to a gait authentication system and method thereof utilizing sensors invariant to sensor rotation and gait dynamic logic implementing an i-vector approach.

Background Information

Gait is the special pattern of human locomotion. It is fairly unique to an individual due to one's specific muscular-skeletal bio-mechanism. Humans can often effortlessly recognize acquaintances by the way they walk or jog. However, as a behavioral biometric, gait may also be affected by transient factors such as tiredness, sickness, emotions, etc. In addition, external factors such as clothes, shoes, carried loads, and ground characteristics influence gait as well.

Automatic gait biometrics, is a field of study that uses gait sensory data and has been an active research area receiving increasing attention over the years. Similar to fingerprint and iris biometrics, gait biometrics can be performed for two purposes: (i) identification, where a gait is compared to a database of enrolled gaits with known identities to determine whom the unknown gait belongs to, and (ii) authentication, where a gait is compared to the enrolled gait data of a known person to validate his or her identity.

In the past decade, accelerometers have been intensely researched for gait and activity analysis. More recently, gyroscopes have also been explored for body motion analysis. These sensors directly measure locomotion when worn on a human body, opening possibilities for highly accurate gait biometrics. With the ubiquity of mobile devices embedded with accelerometers and gyroscopes, motion data can be collected continuously and effortlessly for unobtrusive gait-based authentication and identification as a mere consequence of a user carrying the mobile device around.

Despite a surge in research efforts, gait biometrics using accelerometers and gyroscopes remain a challenge for practical applications due to data dependency on sensor placement: accelerations and rotations are measured along the sensor axis. The measurements change with sensor orientation even when body motion stays the same. Most existing research is conducted in fixed laboratory settings with restricted sensor placement to bypass this problem, and is vulnerable in real-world conditions where the placement of mobile devices is casual and even arbitrary such as in a pocket or in a purse. Although promising results have been reported in well-controlled, even fixed, studies on gait biometrics using accelerometers, there is still a large performance gap between laboratory research and real-world applications.

SUMMARY

Thus, issues continue to exist between gait authentication under real world conditions. A need, therefore, exists for an improved way to conduct gait analysis. The present disclosure addresses these and other issues. Generally, this disclosures presents solutions in overcoming the challenge of sensor orientation dependency in the collection of acceleration and rotation data. In doing so, invariant gait representations are computed that are robust to sensor placement while preserving highly discriminative temporal and spatial gait dynamics and context.

The present disclosure advances the study for gait biometrics using accelerometers and gyroscopes by: (i) directly computing gait features invariant to sensor rotation for robust matching and classification, unlike many existing works which make unrealistic assumptions of fixed sensor placement; (ii) capturing the gait dynamics and motion interactions within gait cycles to be highly discriminative; (iii) adopting the i-vector identity extraction for gait biometrics; (iv) sensibly fusing the accelerometer and gyroscope sensors for gait biometrics, and demonstrate that gyroscopes can be used to boost the gait biometrics accuracy using accelerometers; and (v) enabling high performance realistic gait biometrics for a large population through a combination of the above advancements.

In an exemplary aspect, an embodiment may provide a gait verification system comprising: a mobile computing device configured to be carried by a person while moving with a unique gait; a first sensor carried by the mobile computing device and generating a first signal; a second sensor carried by the mobile computing device and generating a second signal; and gait dynamics logic implementing an identity vector (i-vector) approach to learn feature representations from a sequence of arbitrary feature vectors carried by the first and second signals.

In one exemplary aspect, an embodiment may provide a method comprising the steps of: providing a mobile computing device carrying a first sensor and a second sensor; generating a first signal with the first sensor during a unique gait of a moving person; generating a second signal with the second sensor during the unique gait of the moving person; and computing invariant gait representations that are robust to sensor placement while preserving discriminative temporal and spatial gait dynamics and context.

In another exemplary aspect, an embodiment may provide a method comprising the steps of: providing a mobile computing device carrying a first sensor and a second sensor; generating a first signal with the first sensor during a unique gait of a moving person; generating a second signal with the second sensor during the unique gait of the moving person; and computing invariant gait representations with an identity vector (i-vector) approach, wherein the gait representations are robust to first and second sensor placement and preserve discriminative temporal and spatial gait dynamics; and authenticating (e.g. identifying and verifying) the moving person, based at least in part on, the invariant gait representation computed through an i-vector approach.

BRIEF DESCRIPTION OF THE DRAWINGS

A sample embodiment of the disclosure is set forth in the following description, is shown in the drawings and is particularly and distinctly pointed out and set forth in the appended claims. The accompanying drawings, which are fully incorporated herein and constitute a part of the specification, illustrate various examples, methods, and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 3A is a graph depicting x-axis, y-axis, and z-axis acceleration components from an accelerometer embedded in a mobile phone carried by a walking subject;

FIG. 3B is a graph depicting x-axis, y-axis, and z-axis rotation rate measurements from the embedded gyroscope;

FIG. 3C is a Gait Dynamic Image corresponding to the acceleration feature vectors representing the raw acceleration sequence in FIG. 3A;

FIG. 3D is a Gait Dynamic Image corresponding to the rotational rate feature vectors represent the rotational sequence in FIG. 3B.

DETAILED DESCRIPTION OF THE PREFERRED EMBODIMENT

Figure 1:
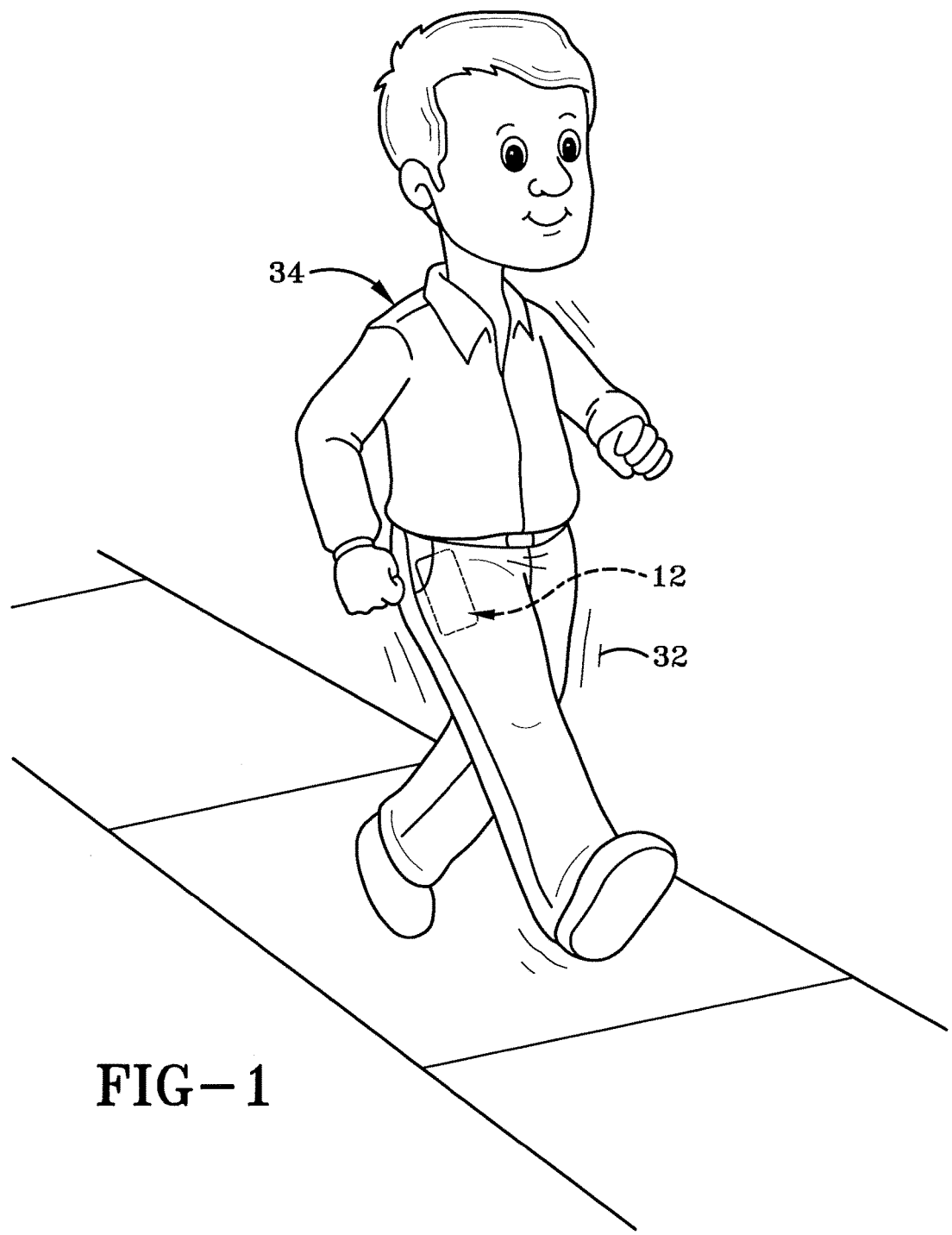
FIG. 1 is a schematic view of a person carrying a mobile computing device having an accelerometer and a gyroscope.
Figure 2:
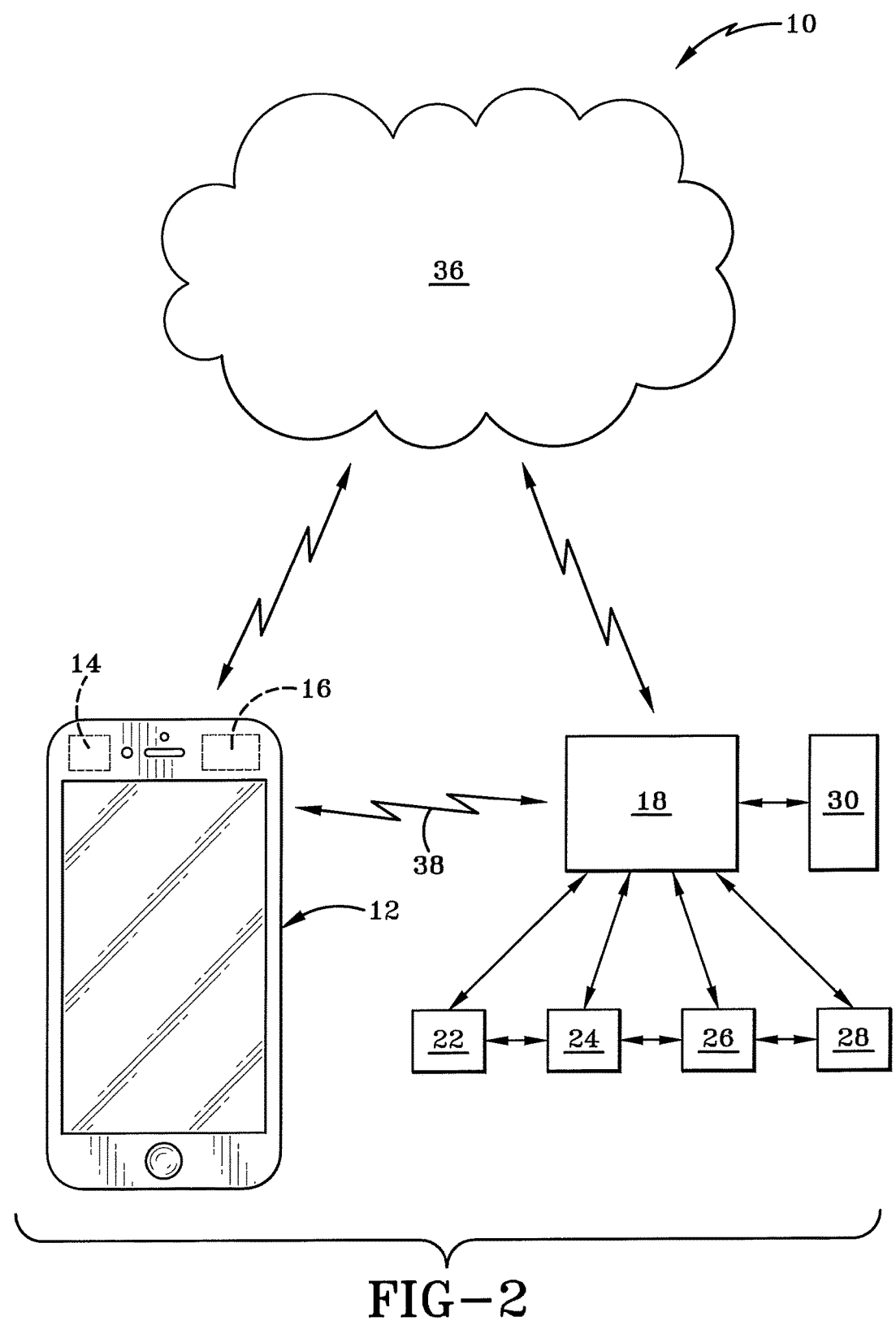
FIG. 2 is a schematic view of a gait authentication system of the present disclosure.

A system and method of gait verification is shown generally throughout FIG. 1 through FIG. 6 and is generally indicated as 10, shown in FIG. 2. Gait verification system 10 may include a mobile computing device 12, a first sensor 14, a second sensor 16, gait dynamics logic 18, a gait dynamic image (GDI) 20, shown in FIG. 4, extraction logic 22, learning logic 24, computation logic 26, modeling logic 28, an index library 30, a gait signature 32 of a moving person 34, and a network 36.

As depicted in FIG. 1, moving person 34 strides forward in a walking, running, or other natural locomotion manner and outputs a unique gait signature 32 that represents the walking gait of person 34 unique to them. Mobile device 12 is carried by moving person 34 in an article of clothing such as a pocket. However, this disclosure is not limited to mobile device 12 being carried in a pocket. It is entirely possible for moving person 34 to carry mobile device 12 on their person in another manner such as in their hand or in a purse or releasably attached by an athletic strap.

As depicted in FIG. 2, mobile computing device 12 is a battery powered and rechargeable electric device preferably implemented as a smartphone. The data analysis pertaining to this disclosure (as discussed in further detail below) was executed and performed on a Nexus 5 smartphone manufactured by LG Electronics and co-developed with and marketed by Google, Inc. having a 2.26 gigahertz quad core. However, one skilled in the art would clearly understand that an alternative smartphone such as a Samsung Galaxy or an Apple iPhone or any other modern smartphone could be utilized as well.

First sensor 14 is integral to mobile device 12 and is electrically powered by the mobile device 12 battery source. In one particular embodiment, first sensor 14 is an accelerometer and may be described throughout the disclosure as accelerometer 14. Second sensor 16 is integral to mobile computing device 12 and is also powered by the battery source. In one particular embodiment, second sensor 16 is a gyroscope and may be referred to throughout this disclosure as gyroscope 16. Accelerometer 14 and gyroscope 16 are sensors ordinarily found in conventional smartphones and do not require additional fabrication or installation to function with a preexisting smartphone or mobile computing device 12.

Accelerometer 14 generates a first signal and gyroscope 16 generates a second signal which may be transmitted over a wireless network connection 36 to gait dynamic logic 18. Alternatively, the first signal generated by accelerometer 14 and the second signal generated by gyroscope 16 may be directly connected to gait dynamic logic 18 via direct connection 38.

"Logic", as used herein, includes but is not limited to hardware, firmware, software and/or combinations of each to perform a function(s) or an action(s), and/or to cause a function or action from another logic, method, and/or system. For example, based on a desired application or needs, logic may include a software controlled microprocessor, discrete logic like a processor (e.g., microprocessor), an application specific integrated circuit (ASIC), a programmed logic device, a memory device containing instructions, an electric device having a memory, or the like. Logic may include one or more gates, combinations of gates, or other circuit components. Logic may also be fully embodied as software. Where multiple logics are described, it may be possible to incorporate the multiple logics into one physical logic. Similarly, where a single logic is described, it may be possible to distribute that single logic between multiple physical logics.

Gait dynamic logic 18 is depicted in FIG. 2 as being external to mobile computing device 12. However, it is to be understood that it is entirely possible that gait dynamic logic 18 may be incorporated into, carried by, and powered electrically by mobile computing device 12. Similarly, extraction logic 22, learning logic 24, computation logic 26, modeling logic 28, and the index library 30 may be incorporated into mobile computing device 12 as well.

As will be described in greater detail below, gait dynamic logic 18 is configured to implement an identity vector (I-vector) approach in order to learn feature representations from a sequence of arbitrary feature vectors representing the gait signature 32 carried by the first and second signals generated by accelerometer 14 and gyroscope 16, respectively, while person 34 moves in a natural locomotion. Gait dynamic logic 18 is electrically connected to extraction logic 22 and able to send and transmit signals therebetween. Extraction logic 22 is electrically connected to learning logic 24 and able to send electric signals therebetween. Learning logic 24 is electrically connected to gait dynamics logic 18 and able to send signals therebetween. Learning logic 24 is electrically connected to computation logic 26 and able to send electric signals therebetween. Computation logic 26 is also electrically connected to gait dynamics logic 18 and able to send electric signals therebetween. Computation logic 26 is electrically connected to modeling logic 28 and able to send signals therebetween. Modeling logic 28 is electrically connected to gait logic 18 and able to send signals therebetween. With respect to extraction logic 22, learning logic 24, computation logic 26, and modeling logic 28, the disclosed arrangement is merely for descriptive purposes and one having ordinary skill in the art would clearly understand that these logics may be combined into a single logic or they may be rearranged in alternative orders provided that they accomplish the implementation of gait signature analysis of feature vectors generated from the first signal of accelerometer 14 and generated from the second signal of gyroscope 16 as will be described in greater detail below in the operational description of system 10.

Learning logic 24 learns the feature representations from the sequence of arbitrary feature vectors in the first and second signals generated from the sensors 14, 16. Computation logic 26 uses feature representations learned from the learning logic 24 to calculate at least one of the following: (i) vector distance similarity measurements, (ii) input measurements to an additional feature transform modelling, and (iii) input measurements to an additional machine learning modelling.

Modeling logic 28 may build a universal background model by pooling at least some of the feature vectors from a training data set (which may be contained in index library 30 or another location) and to compute a supervector for each authentication GDI feature sequence. Additionally, modeling logic 28 may include a curve estimation logic to fit smooth horizontal curves across one GDI to maximize overall intensity.

Index library 30 may have a memory to store a variety of digital representation of gait signatures, such as GDIs 20, for later retrieval by gait dynamics logic 18 through a direct connection or by computing device 12 through a wireless connection or direction connection. Additionally, library 30 may store (i) identification data in a database of enrolled gaits with known identities to determine whom an unknown gait belongs to, and (ii) authentication data in a database of enrolled gait data of a known person to validate/verify (e.g. verification) his or her identity.

As depicted in FIG. 3A, acceleration measurements from accelerometer 14 are depicted in a line graph representing directional accelerations in movement of the accelerometer 14 along its x-axis 40, its y-axis 42, and its z-axis 44. During a first locomotion pattern 46, the person 34 is moving forward with having a unique gait signature 32. During the first locomotion pattern 46, accelerometer 14 generates the first signal carrying and depicting the repetitively uniform acceleration feature vectors of the x-axis 40. Similar acceleration feature vectors are repetitively uniform for y-axis 42 and z-axis 44 during the first locomotion pattern 46. Pattern 48 of FIG. 3A represents an instance when person 34 is moving forward but mobile computing device 12 carrying accelerometer 14 is moved or otherwise shifted (this may be referred to as a shifting motion or a shifting pattern or a repositioning pattern). One exemplary shifting motion during repositioning pattern 48 is when a user reaches into their pocket and slightly moves their cell phone or mobile computing device 12 such that the computing device 12 is in a different position after being touched by the person 34. During the repositioning pattern 48, the acceleration vectors representing x-axis 40, y-axis 42, and z-axis 44 are non-uniform and disjointed representing an irregular movement and not representing the unique gait of person 34. After repositioning the mobile computing device 12, a second locomotion pattern 50 is represented where the acceleration vectors representing x-axis 40, y-axis 42, and z-axis 44 return to a repeatably uniform sequence capable of creating a GDI 20 therefrom. The creation of GDI 20 from line data of x-axis 40, y-axis 42, and z-axis 44 will be described in greater detail below.

FIG. 3B similarly represents data obtained from 3 axes during the first locomotion pattern 46, during the repositioning pattern 48, and during a second locomotion pattern 50. FIG. 3B depicts the rotational vector data from x-axis 52, y-axis 54, and z-axis 56 obtained from gyroscope 16. During first locomotion pattern 46, x-axis 52, y-axis 54, and z-axis 56 produce repeatably uniform digital data sequences. During repositioning 48, gyroscope 16 and its x-axis 52, y-axis 54, and z-axis 56 are non-uniform and irregular depicting a scattering effect as mobile computing device 12 is repositioned within the pocket of moving person 34. After mobile computing device 12 has been repositioned at pattern 48 and the second locomotion pattern 50 continues and the x-axis 52, y-axis 54, and z-axis 56, data of gyroscope 16 returns to a repeatably uniform sequence to which a GDI 20 can be extracted.

Both sensors 14, 16 capture distinguishing locomotion patterns characteristic of a person's gait 32. However, as the moving person 34 repositions the sensor (i.e., reposition pattern 48), the captured gait patterns change drastically due to data dependency on sensor orientation.

As depicted in FIG. 3C, a GDI 20 is represented. More particularly, a first GDI 20A corresponds to the acceleration components of x-axis 40, y-axis 42, and z-axis 44 of accelerometer 14 during first locomotion pattern 46, repositioning pattern 48, and during second locomotion pattern 50, respectively.

FIG. 3D corresponds with the gyroscope 16 data represented in FIG. 3B. Particularly, a second GDI 20B is produced from the gyroscope component x-axis 52, y-axis 54, and z-axis 56 during first locomotion pattern 46, during the repositioning pattern 48, and during the second locomotion pattern 50.

As depicted in FIG. 3C and FIG. 3D, during the first locomotion pattern 46 and during the second locomotion pattern 50, the respective GDI's 20A, 20B have generally uniform image patterns. Stated otherwise, in first GDI 20A, the image pattern represented in during the first locomotion pattern 46 time segment is generally uniform and symmetrical for the first locomotion pattern 46. Additionally, the image obtained during second locomotion pattern 50 is generally uniform and symmetrical for the second locomotion pattern 50. The image section generated in during the repositioning pattern 48 of FIG. 3C of first GDI 20A is irregular and non-uniform and non-symmetrical indicating a shifting of mobile computing device 12 carrying accelerometer 14.

FIG. 3D depicts a second GDI 20B having a generally uniform and symmetrical image section in during the first locomotion pattern 46 and an image pattern that is generally symmetrical and uniform in the second locomotion pattern 50. During the repositioning pattern 48, the image created by gyroscope 16 in FIG. 3D is generally non-uniform and non-symmetrical representing the repositioning of mobile computing device 12 carrying gyroscope 16.

In the GDI 20A in FIG. 3C and the GDI 20B in FIG. 3D, the gravity component is removed from the acceleration time series before the computation of GDIs. The GDIs are invariant to sensor orientation and thus show much better consistency before and after the sensor re-positioning.

Figure 4A:
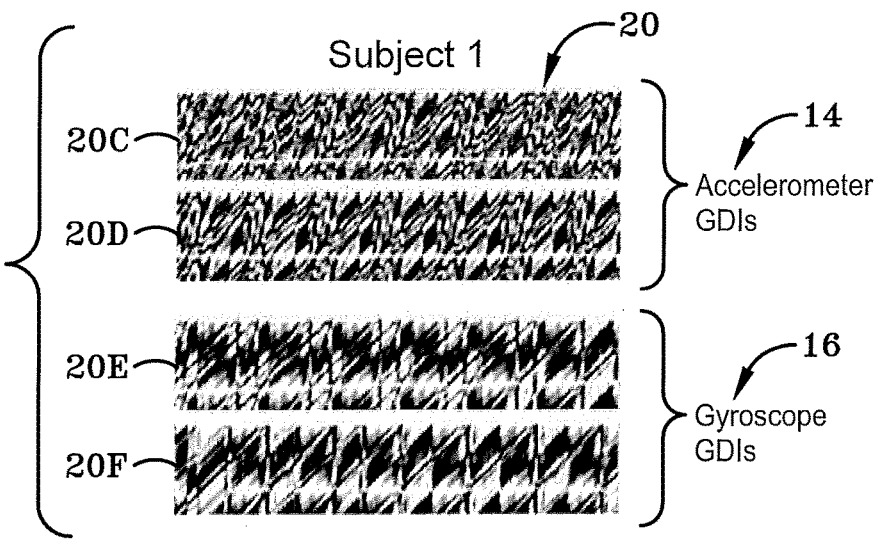
FIG. 4A depicts acceleration gait dynamic images and gyroscope gait dynamic images for a first subject.
Figure 4B:
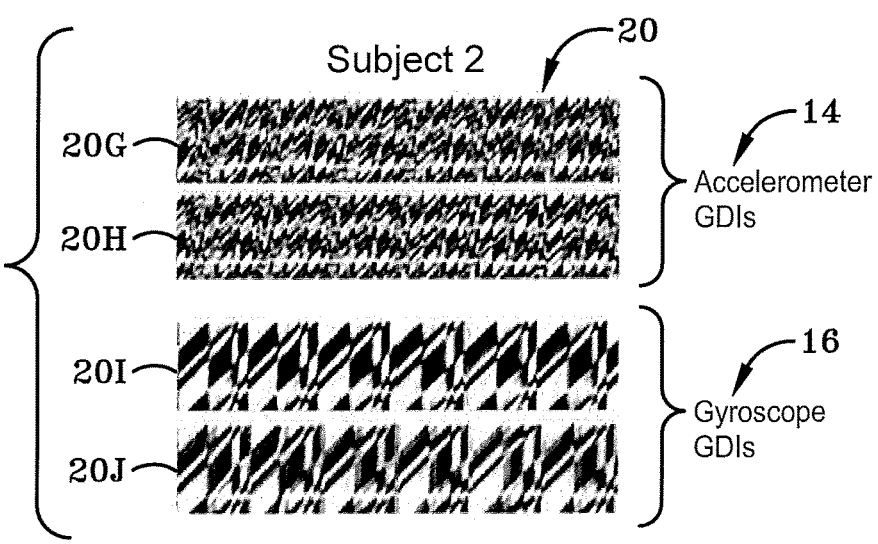
FIG. 4B depicts acceleration gait dynamic images and gyroscope gait dynamic images for a second subject.
Figure 4C:
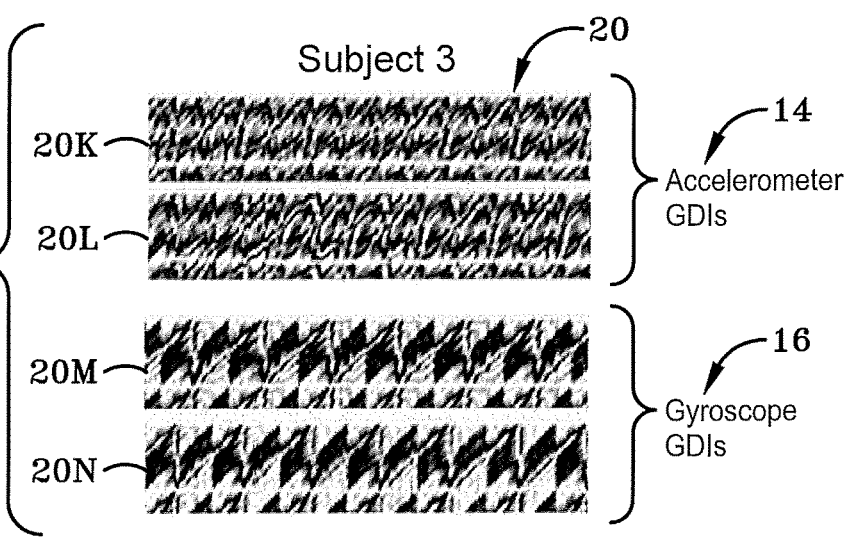
FIG. 4C depicts acceleration gait dynamic images and gyroscope gait dynamic images for a third.

As depicted in FIG. 4A, FIG. 4B, and FIG. 4C, a plurality of GDIs 20 are shown for a first subject (i.e., Subject 1), a second subject (i.e., Subject 2), and a third subject (i.e., Subject 3), respectively. These images exhibit high intra-subject consistency and notable/remarkable inter-subject distinctions despite of sensor orientation variations.

More particularly, in FIG. 4A, one exemplary GDI 20C and another exemplary GDI 20D represent GDIs obtained from accelerometer 14 for a first subject labeled "Subject 1." There is high consistency between the two accelerometer GDIs 20C, 20D for Subject 1. With continued reference to FIG. 4A, one exemplary GDI 20E and another exemplary GDI 20F represent GDIs obtained from gyroscope 16 for Subject 1. There is high consistency between the two gyroscope GDIs 20E, 20F for Subject 1.

In FIG. 4B, one exemplary GDI 20G and another exemplary GDI 20H represent GDIs obtained from accelerometer 14 for a second subject labeled "Subject 2." There is high consistency between the two accelerometer GDIs 20G, 20H for Subject 2. With continued reference to FIG. 4B, one exemplary GDI 20I and another exemplary GDI 20J represent GDIs obtained from gyroscope 16 for Subject 2. There is high consistency between the two gyroscope GDIs 20I, 20J for Subject 2.

In FIG. 4C, one exemplary GDI 20K and another exemplary GDI 20L represent GDIs obtained from accelerometer 14 for a third subject labeled "Subject 3." There is high consistency between the two accelerometer GDIs 20K, 20L for Subject 3. With continued reference to FIG. 4C, one exemplary GDI 20M and another exemplary GDI 20N represent GDIs obtained from gyroscope 16 for Subject 3. There is high consistency between the two gyroscope GDIs 20M, 20N for Subject 3.

Figures 5, 6:
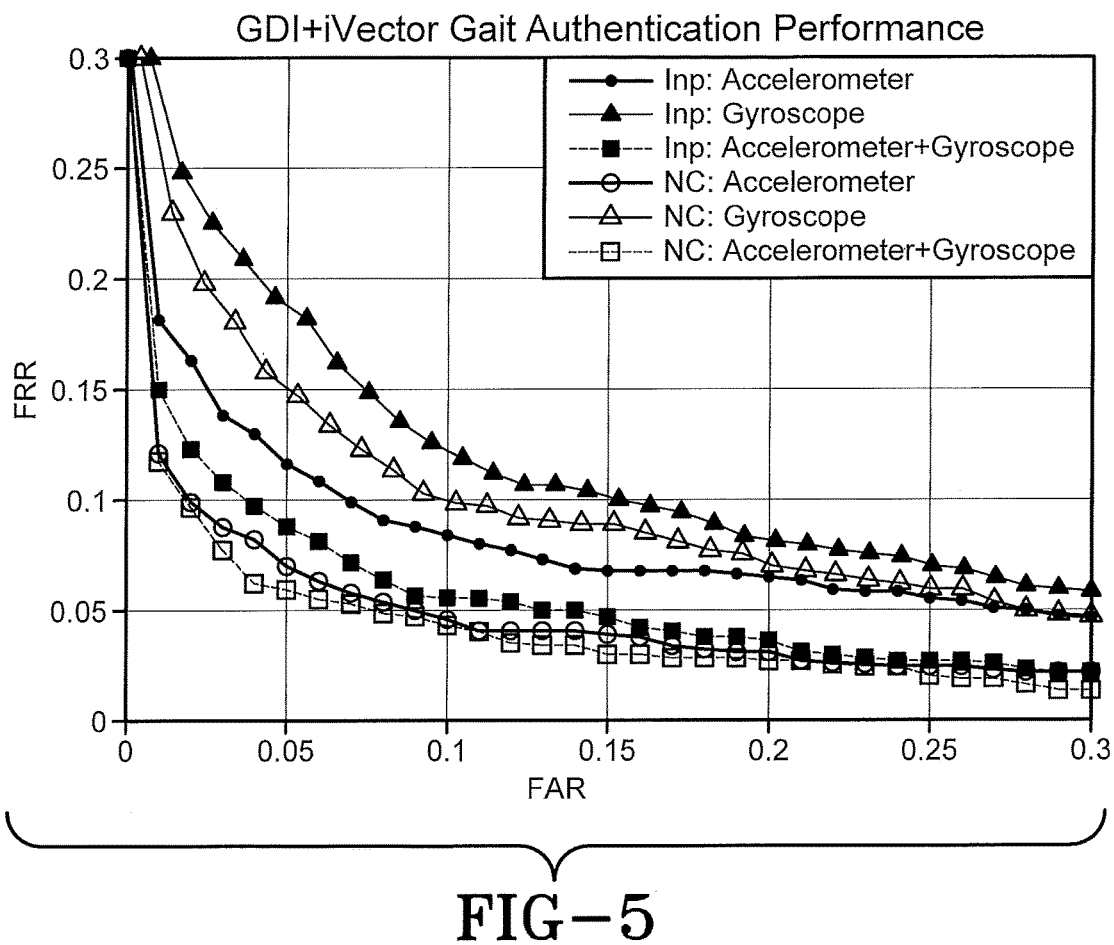
FIG. 5 is a graphical plotting detailing I-vector gait authentication results on a 744-subject Osaka University gait dataset, using inner product GDIs (lnp) and cosine similarity GDIs (NC) from accelerometer, gyroscope and sensor fusion.
FIG. 6 is a Table present sensor modality information for each sensor based on previous approaches and the approach utilized in the present disclosure.

FIG. 5 provides a graphical plotting of I-vector gait authentication results on a 744-subject Osaka University gait dataset, using inner product GDIs (Inp) and cosine similarity GDIs (NC) from accelerometer 14, gyroscope 16 and sensor fusion. The authentication results are plotted in FIG. 5 to show the tradeoffs between the false rejection rate (FRR) and the false acceptance rate (FAR).

As depicted in FIG. 6, a table displays Gait authentication performance by displaying equal error rates (EER in %) of an Osaka Univeristy gait dataset containing 744 subjects. The Table in FIG. 6 compares EERs of two algroriths associated with the present disclosure, which are indicated on the bottom two rows: using inner product GDIs (Inp GDI) 68 combined with i-vector modeling and using cosine similarity GDIs (NC GDI) 70 combined with i-vector modeling. The table in FIG. 6 depicts the EERs for the four published algorithms using the same dataset, namely the Gafurov et. al. reference 60 [D. Gafurov, E. Snekkenes, and P. Bours. Spoof attacks on gait. IEEE Transactions on Information Forensics and Security, Special Issue on Human Detection and Recognition, 2007], the Derawi et. al. reference 62 [M. O. Derawi, P. Bours, and K. Holien. Improved cycle detection for accelerometer based gait authentication. In Intelligent Information Hiding and Multimedia Signal Processing (IIH-MSP), Sixth International Conference, 2010], the Liu et. al. reference 64 [Z. Liu and S. Sarkar, "Improved gait recognition by gait dynamics normalization," IEEE Trans. Pattern Anal. Mach. Intell., vol. 28, no. 6, pp. 863-876, June 2006], and the Ngo et. al. reference 66 [Ngo Thanh Trung, Makihara, Y.; Nagahara, H.; Mukaigawa, Y.; Yagi, Y.; "Performance evaluation of gait recognition using the largest inertial sensor-based gait database", in Biometrics (ICB), 2012 5th IAPR International Conference on Biometrics Compendium, IEEE, on Mar. 29, 2012 to Apr. 1, 2012].

In accordance with the gait authentication system 10 described above, system 10 provides advantages to solve the issues that continue to exist for gait authentication under real world conditions. Namely system 10 and method thereof overcomes the challenge of sensor orientation dependency in the collection of acceleration and rotation data by computing invariant gait representation that are robust to sensor placement while preserving highly discriminative temporal and spatial gait dynamics and context. System 10 overcomes the issues that continue to exist for gait authentication under real world conditions gait biometrics using accelerometers 14 and gyroscopes 16 by: (i) directly computing gait features invariant to sensor rotation for robust matching and classification, unlike many existing works which make unrealistic assumptions of fixed sensor placement; (ii) capturing the gait dynamics and motion interactions within gait cycles to be highly discriminative; (iii) adopting the i-vector identity extraction, a prominent speaker authentication approach, for gait biometrics; (iv) sensibly fusing (i.e., system fusion 72) the accelerometer and gyroscope sensors for gait biometrics, and demonstrate for the first time that gyroscopes can be used to boost the gait biometrics accuracy using accelerometers; and (v) enabling high performance realistic gait biometrics for a large population through a combination of the above advancements. Reference will now be made to the operation of system 10 and its method.

Invariant Gait Representation

One of the major challenges for mobile device based gait biometrics (i.e., gait authentication, gait identification, and gait verification) is the data dependency on sensor orientation. In some instances the sensors must be oriented relative to the ground or relative to a fixed bearing, however providing that dependent relation under real world conditions proves difficult.

In operation and as depicted in FIG. 3A and FIG. 3B, the accelerometer 14 and gyroscope 16 carried by mobile device 12 generate signals during the first pattern 46 and the second pattern 48, respectively. The data contained in the first and second signals is collected by various logics (FIG. 2) before (i.e., first pattern 46) and after (i.e., first pattern 50) a sensor (or device) rotation at reposition pattern 48. As depicted, the line graphs of FIGS. 3A and 3-B differ drastically when comparing the graphical shape of first pattern 46 with the graphical shape of second pattern 50. The difference makes gait matching a challenging task.

For realistic mobile gait biometrics, the device 12 placement is casual and unconstrained, such as in a pocket of moving person 34. Thus, the system 10 and the method of system 10 provides essential extraction features that are robust to the sensor rotation.

The operation of gait authentication system 10 solves the aforementioned issues by utilizing gait features that characterize the distinguishing locomotion gait signature 32 while staying invariant to first and second sensor 14, 16 orientation.

While the individual acceleration data (FIG. 3A) does depend on sensor placement, it is possible to extract relationships between a pair of observations from one sensor that does not (i.e. gyroscope 16 does depend on sensor placement). Subsequently, gait specific features are computed using these pairwise interactions inside each gait cycle to capture the gait dynamics via gait dynamics logic 18, resulting in discriminative and robust representations for gait analysis.

A gait representation image that is invariant to sensor orientation that is called a Gait Dynamics Image (GDI), for gait biometrics and also for general motion analysis using 3D acceleration data from accelerometers 14. Additionally, the sensor rotation invariant GDIs were extracted for rotation data captured by gyroscopes 16 for gait biometrics and motion analysis in general. Example GDIs computed for accelerometer and gyroscope data are shown in FIG. 4A, FIG. 4B, and FIG. 4C.

In operation and with reference to FIG. 4A, FIG. 4B, and FIG. 4C, these GDIs exhibit good intra-subject consistency and notable inter-subject distinctions despite of sensor orientation variations. Stated otherwise, the GDIs acquired from accelerometer 14 for subject 1 are closely similar, meaning their intra-subject consistency is high. However, it is clear that the GDIs obtained by accelerometer 14 for subject 2 are no similar to subject 1. This means that there is high inter-subject inconsistency.

GDIs 20 encode both dynamics for the time series and the local interactions. Given the irregular periodic input locomotion time series, gait dynamics images 20 also display quasi-periodicity in both the time and time lag domains with the period approximating the length of a gait cycle.

As shown in FIG. 4A, FIG. 4B, and FIG. 4C, these GDI images (20C through 20N), when the time lag coincides with the length of the local gait cycle, the GDI features have high values as signals repeat themselves. This is reflected by horizontal lines of high similarity measurements in both GDIs, starting with the first row, repeating at the length of a gait cycle. Gait cycles can be estimated via modeling logic 28 by fitting smooth horizontal curves across the image which maximizes the overall intensities. Due to the quasi-periodic nature of gait and the repetitive pattern in GDIs, arbitrary length L (described in greater detail below) is set to be slightly greater than the length of average gait cycles to preserve all contexts within a gait cycle when computing GDIs.

I-Vector Utilization

The i-vector method/approach was originally developed in the domain of speaker recognition research. It is a method and approach to learn a new compact low dimensional feature representation given a sequence of arbitrary feature vectors. For example, in the speech domain, the feature representation was the speech pattern of a person talking. This i-vector learning is typically conducted in an unsupervised fashion based on data from a large pool of subjects. The learned new feature vector can then be used to either perform simple vector distance based similarity measure or as input to any further feature transform or machine learning modelling. The measurements are then coupled with some electronic circuitry or logic to authenticate or verify or identify the person.

Some exemplary non-limiting advantages of i-vector approach are: (i) that it can be applied to any type of raw input feature; (ii) it can convert input sequence of any length to a fixed low dimension feature vector, thus enable compact model size and very fast matching; (iii) it performs factor analysis in a built in step of i-vector training, it helps to remove many confounding factors in biometric analysis and extract a unique identity feature vector; and (iv) the i-vectors can be further processed with any existing discriminative feature transform and machine learning method.

Until now and upon information and belief, the i-vector approach was not used in the field of gait biometric or gait pattern machine learning. The method of system 10 introduces the i-vector approach to the field of gait pattern machine learning and to the domain of gait biometric extraction and matching, and is detailed further below.

Gait Classification Using GDIs and I-Vector

In operation, system 10 and the method of system 10 includes the i-vector approach/model to classify GDIs 20 for gait biometrics. I-vector approach for system 10 extracts subject specific signatures from sensory data corrupted with variations from various irrelevant sources. The i-vector extraction method for system 10 uses total variability factor analysis provides an appealing solution to gait identity extraction using GDIs 20.

The following steps are a method for the i-vector extraction procedure. The i-vector modeling for user authentication may include four primary steps, which of course, may have further sub-steps. The steps are:

Step 1. Building a universal background model (UBM) using a Gaussian mixture model (GMM) by pooling all or a subset of the feature vectors from the training data set. Note that the raw GDI features are enhanced with additional delta GDI features.

Step 2. Given the trained UBM ($\Omega$), computing a supervector for each enrollment or authentication gait GDI feature sequence of L frames $\{y_1, y_2, \ldots, y_L\}$, where each frame is a feature vector of dimension F:

i. the posterior probability ($N_c$) and Baum-Welch statistics ($\tilde{F}_c$) for each Gaussian component are computed as:

$$N_c = \Sigma_{t=1}^{L} O(c|y_t, \Omega), \qquad \text{(Equation 1)}$$

and $$\tilde{F}_c = \Sigma_{t=1}^{L} P(c|y_t, \Omega)(y_t - m_c), \qquad \text{(Equation 2)}$$

where $m_c$ is mean vector for Gaussian component c.

and ii. The supervector M is obtained by concatenating $\tilde{F}_c$ for all Gaussian components to form a vector of fixed dimension C·F for an input sequence of arbitrary length L.

Step 3. Conducting factor analysis in the supervector space using a simplified linear model:

$$M = m + Tw \qquad \text{(Equation 3)}$$

where m is a subject independent component, T is a low rank rectangular matrix, and w is the i-vector. The training process learns the total variability matrix T and a residue variability covariance matrix $\Sigma$. The i-vector is then computed as:

$$w = (I + T^t \Sigma^{-1} NT)^{-1} T^t \Sigma^{-1} M, \qquad \text{(Equation 4)}$$

where N is a diagonal matrix consisting of diagonal blocks of $N_c I$.

Step 4. Once an i-vector is extracted for each gait sequence, the similarity between two gait sequences is then computed as the cosine distance between their corresponding i-vectors:

$$d(w_1, w_2) = \frac{<w_1, w_2>}{\|w_1\| \|w_2\|} \qquad \text{(Equation 5)}$$

Performance Analysis

The analysis of system 10 and its gait biometrics algorithm utilized the largest publicly available gait dataset; the Osaka University (Japan) dataset which consists of 744 subjects with both gyroscope and accelerometer data. In this dataset, each subject has two walking sequences—one for training and one for testing. On average, each training gait sequence is 5.3 seconds, and each testing gait sequence is 4.2 seconds.

The method of system 10 applies the i-vector approach in learning the GDI feature sequence for gait identity vector extraction. The details of the system setup are as follows: The UBM was built by a GMM of 800 components. This is achieved by first training a GMM with diagonal covariance matrixes and then using the trained model to initialize and train a full covariance GMM. The posterior probability and super-vectors are then constructed for each gait sequence. The factor analysis model is then trained with five iterations of expectation and maximization (EM) algorithm. The factor analysis matrix transforms each high dimensional supervector to a compact low dimension i-vector. The i-vector dimensions were chosen to be 60 and 40 for the accelerometer 14 and the gyroscope 16 modality, respectively.

The method of system 10 then applies the cosine similarity scores of i-vectors to perform authentication. The method of system 10 conducted an exhaustive 744×744 authentication tests using the i-vector modeling tool. No effort was made to the i-vector similarity score normalization before applying a single threshold to the 744×744 scores to compute the equal error rates (EERs) for each sensor modality.

Further, the method of system 10 reduced the EERs by sensor fusion using the average score from the two modalities of accelerometer 14 and gyroscope 16. The authentication results are plotted in FIG. 5 to show the tradeoffs between the false rejection rate (FRR) and the false acceptance rate (FAR). The normalization effect in cosine similarity GDIs appears to be beneficial as they outperform inner product GDIs for both sensor modalities and also for the fusion case. The performance gain of sensor fusion are significant for both types of GDI features.

The method of system 10 then compares the performances of the proposed algorithms to four existing gait authentication algorithms. As shown in the Table of FIG. 6, GDI+i-vector approach to gait authentication has resulted in significant lower EERs, compared with published results (references 60, 62, 64, and 66) on the same data set of 744 subjects, using the same training and testing subsets. In addition, FIG. 6 depicts a system fusion 72 by averaging the scores of Inp GDI i-vector system 68 and NC GDI i-vector system 70. This system fusion 72 resulted in significant error rate reduction. The method of system 10 reduced the EER by more than half compared to the best published results.

In operation and with respect to the Table in in FIG. 6, gait authentication performance (EER in %) on the Osaka University gait dataset containing 744 subjects. The method of system 10 compares EERs of the proposed algorithm (bottom two rows: using inner product GDIs (Inp GDI) and cosine similarity GDIs (NC GDI) combined with i-vector modeling) with those of four published algorithms (Top four rows, as reported in, Table 2, namely references 60, 62, 64, and 66) using the same dataset.

The method of system 10 implemented the gait sequence i-vector extraction and authentication algorithms on a Nexus 5, 2.26 GHz quad-core smartphone. The average running time to extract a i-vector on the phone is 0.11 second, given the input gait length of 4.2 seconds. Thus, this approach can achieve real-time computation on most COTS mobile devices.

Additional Matters

Gait authentication system 10 and the method of system 10 provides invariant gait representations called GDIs for accelerometer 14 and gyroscope 16 sensory data. GDIs are robust to variations in sensor orientation. GDIs are also invariant to symmetry transforms of the motion measurements. As the bilateral symmetry in human bodies often result in symmetric locomotion for the left and right side of the body, system 10 and the method of system 10 enables the matching of GDIs 20 computed using a device 12 placed in one pocket to GDIs 20 computed from a device 12 carried in a corresponding pocket on the other side. These invariant properties of GDIs 20 greatly relax the sensor 14, 16 placement restrictions on device 12 for realistic mobile gait biometrics. GDIs 20 are highly informative and discriminative by encoding fine scale intrinsic interactions and complex dynamics within gait cycles to enable high performance gait authentication for a large user population. With these two advancements combined by system 10 and the method of system 10, GDIs 20 offer mobile device 12 users a promising gait representation allowing for robust and accurate gait biometrics in their daily lives.

While the present disclosure has been described in connection with the preferred embodiments of the various figures, it is to be understood that other similar embodiments may be used or modifications or additions may be made to the described embodiment for performing the same function of the present disclosure without deviating therefrom. Therefore, the present disclosure should not be limited to any single embodiment, but rather construed in breadth and scope in accordance with the recitation of the appended claims.

The term authentication used herein refers to all types of gait biometrics that can be used to verify (i.e. gait verification) or identify (i.e. gait identification) an individual moving under human locomotion patterns.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the preferred embodiment of the disclosure are an example and the disclosure is not limited to the exact details shown or described.

What is claimed is:

1. A gait authentication system comprising:
   a mobile computing device configured to be carried by a person while moving with a unique gait;
   a first sensor carried by the mobile computing device and generating a first signal;
   a second sensor carried by the mobile computing device and generating a second signal;
   gait dynamics logic implementing an identity vector (i-vector) approach to learn feature representations from a sequence of arbitrary feature vectors carried by the first and second signals;
   a gait dynamic image (GDI) generated from the feature representations; and
   extraction logic to extract gait specific signatures unique to the moving person from observed sensory data in the first and second signals generated from the first and second sensors, wherein the first and second signals include a plurality of irrelevant data.

2. The gait authentication system of claim 1, further comprising:

a plurality of GDIs, wherein the GDIs are invariant relative to a physical orientation of the first and second sensors and adapted to present consistent images before and after repositioning the mobile device.

3. The gait authentication system of claim 1, further comprising:
a gait signature representing locomotion pattern of the person moving with a unique gait;
wherein the gait signature characterizes the unique gait of the person invariantly relative to position of the first and second sensors.

4. The gait authentication system of claim 1, further comprising:
an independent relationship between the first signal and the second signal, wherein the gait dynamics logic captures gait dynamics in each gait cycle of the moving person the independent relationship between the first and second signals.

5. The gait authentication system of claim 1, further comprising:
learning logic to learn the feature representations from the sequence of arbitrary feature vectors.

6. The gait authentication system of claim 5, further comprising:
computation logic using the feature representations learned from the learning logic to calculate at least one of (i) vector distance similarity measurements, (ii) input measurements to an additional feature transform modelling, and (iii) input measurements to an additional machine learning modelling.

7. The gait authentication system of claim 6, further comprising:
modeling logic to build a universal background model (0) by pooling at least some of the feature vectors from a training data set and to compute a supervector for each authentication GDI feature sequence.

8. The gait authentication system of claim 7, further comprising curve estimation logic to fit smooth horizontal curves across one GDI to maximize overall intensity.

9. The gait authentication system of claim 8, wherein any one of the modeling logic, estimation logic, computation logic, and the gait dynamics logic analyzes a supervector for each enrollment or authentication gait GDI feature sequence of L frames $\{y_1, y_2, \ldots, y_L\}$, where each frame is a feature vector of dimension F; and
the posterior probability ($N_c$) and Baum-Welch statistics ($\tilde{F}_c$) for each Gaussian component are computed as:

$$N_c = \Sigma_{t=1}^{L} P(c|y_t, \Omega), \quad \text{(Equation 1)}$$

and $$\tilde{F}_c = \Sigma_{t=1}^{L} P(c|y_t, \Omega)(y_t - m_c), \quad \text{(Equation 2)}$$

where $m_c$ is mean vector for Gaussian component c; and
a supervector M is obtained by concatenating $\tilde{F}_c$ for all Gaussian components to form a vector of fixed dimension C·F for an input sequence of arbitrary length L.

10. The gait authentication system of claim 9, wherein the same logic implementing Equation 1 and Equation 2 conducts factor analysis in the supervector space using a simplified linear model:

$$M = m + Tw \quad \text{(Equation 3)}$$

where m is a subject independent component, T is a low rank rectangular matrix, and w is the i-vector.

11. The gait authentication system of claim 10, wherein the same logic implementing Equation 1, Equation 2, and Equation 3 computes an i-vector as:

$$w = (I + T^t \Sigma^{-1} NT)^{-1} T^t \Sigma^{-1} M, \quad \text{(Equation 4)}$$

where N is a diagonal matrix consisting of diagonal blocks of $N_c I$.

12. The gait authentication system of claim 11, wherein once the i-vector is extracted for each gait sequence, the computation logic computes a similarity between two gait sequences as the cosine distance between two corresponding i-vectors according to:

$$d(w_1, w_2) = \frac{<w_1, w_2>}{\|w_1\|\|w_2\|}. \quad \text{(Equation 5)}$$

13. A method comprising the steps of:
providing a mobile computing device carrying a first sensor and a second sensor, wherein the first sensor is an accelerometer and the second sensor is a gyroscope;
generating a first signal with the first sensor during a unique gait of a moving person;
generating a second signal with the second sensor during the unique gait of the moving person; and
computing invariant gait representations with an identity vector (i-vector) approach, wherein the gait representations are robust to the first sensor placement and the second sensor placement and preserve discriminative temporal and spatial gait dynamics;
authenticating the moving person, based at least in part on, the invariant gait representation computed through an i-vector approach;
creating a first gait dynamics image (GDI) from acceleration measurements obtained in the first sensor;
creating a second GDI from rotational measurement obtained in the second sensor; and
learning a GDI feature sequence for later gait identity vector extraction.

14. The method of claim 13, wherein the step of computing invariant gait representations with an i-vector approach further comprises the step of:
computing a gait specific feature, based at least in part on, pairwise interactions inside each gait cycle.

15. The method of claim 14, wherein the step of computing invariant gait representations with an i-vector approach further comprises the step of:
encoding dynamics for a time series and encoding dynamics for local interactions in the GDI.

16. The method of claim 13, further comprising the step of:
extracting signatures of the unique gait of the moving person from sensory data corrupted with variations from various irrelevant sources.

17. The method of claim 16, further comprising the step of:
building a universal background model (UBM) using a Gaussian mixture model (GMM) by pooling all or a subset of a set feature vectors from a training data set.

18. The method of claim 17, further comprising the step of:
computing a supervector for each enrollment or authentication gait GDI feature sequence.

19. The method of claim 18, further comprising the step of:
conducting factor analysis for the supervector utilizing a simplified linear mode.

20. The method of claim 19, further comprising the step of:
  computing the similarity between two gait sequences as the cosine distance between their corresponding i-vectors.

21. The method of claim 20, wherein the step of authenticating is accomplished by applying cosine similarity scores of i-vectors against a set of known indexes to authenticate the moving person.

\* \* \* \* \*